United States Patent [19]

Heywang et al.

[11] Patent Number: 4,616,035
[45] Date of Patent: * Oct. 7, 1986

[54] PESTICIDALLY ACTIVE NOVEL N-OXALYL DERIVATIVES OF N-METHYLCARBAMATES

[75] Inventors: Gerhard Heywang; Engelbert Kühle, both of Bergisch-Gladbach; Bernhard Homeyer, Leverkusen, all of Fed. Rep. of Germany

[73] Assignee: Bayer Aktiengesellschaft, Leverkusen, Fed. Rep. of Germany

[ * ] Notice: The portion of the term of this patent subsequent to Mar. 26, 2002 has been disclaimed.

[21] Appl. No.: 661,008

[22] Filed: Oct. 15, 1984

[30] Foreign Application Priority Data

Oct. 18, 1983 [DE] Fed. Rep. of Germany ....... 3337858

[51] Int. Cl.$^4$ ................ A01N 47/22; C07D 307/86
[52] U.S. Cl. .................... 514/469; 514/234;
514/255; 514/320; 514/422; 514/452; 514/463;
514/464; 514/465; 544/153; 544/376; 546/196;
548/425; 549/365; 549/366; 549/370; 549/435;
549/448; 549/470
[58] Field of Search ............... 549/470, 435, 448, 370;
514/469, 255, 320, 234, 422, 463, 452, 464, 465;
548/425; 546/196; 544/153

[56] References Cited

U.S. PATENT DOCUMENTS 4,014,923 3/1977 Kühle et al. .................... 560/32
4,507,292 3/1985 Heywang et al. ................ 549/470

FOREIGN PATENT DOCUMENTS 2132936 1/1973 Fed. Rep. of Germany .
2142496 3/1973 Fed. Rep. of Germany .
3205195 8/1983 Fed. Rep. of Germany .

Primary Examiner—Henry R. Jiles
Assistant Examiner—Bernard I. Dentz
Attorney, Agent, or Firm—Sprung Horn Kramer & Woods

[57] ABSTRACT

Combating pests such as insects, arachnids and nematodes with novel N-oxalyl-N-methylcarbamic acid esters of the formula

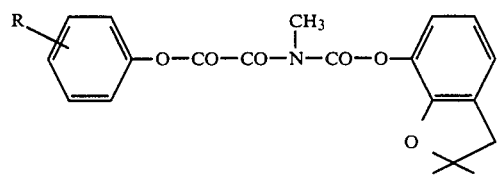

in which R represents alkyl, alkenyl, alkinyl, alkoxy, alkylthio, halogenoalkyl, halogenoalkoxy, halogenalkylthio, halogen, nitro, dialkylamino, alkylsulphinyl, alkylsulphonyl, cycloalkyl or a saturated, optionally substituted heterocyclic radical with one or more hetero-atoms from the group comprising O, S and N, or forms a ring which is fused onto the phenyl radical, optionally contains one or more hetero-atoms from the group comprising O, S and N and is optionally substituted.

8 Claims, No Drawings

PESTICIDALLY ACTIVE NOVEL N-OXALYL DERIVATIVES OF N-METHYLCARBAMATES

The present invention relates to N-oxalyl derivatives of methylcarbamates, a process for their preparation and their use as agents for combating pests.

It has already been disclosed that N-carboxylated aryl N-methylcarbamates (compare DE-OS (German Published Specification) No. 2,132,936 corresponding to U.S. Pat. No. 4,014,923), aryl N-chlorocarbonyl-N-methyl-carbamates (compare DE-OS (German Published Specification) No. 2,142 496) and aryl N-oxlyl-N-methylcarbamates compare DE-OS (German Published Specification) No. 3,205,195 corresponding to, U.S. application Ser. No. 461,368 filed Jan. 27 1983 now U.S. Pat. No. 4,507,292) have insecticidal properties. However their action is not always completely satisfactory, especially when low amounts are applied.

New N-oxalyl-N-methyl-carbamic acid esters of the formula I

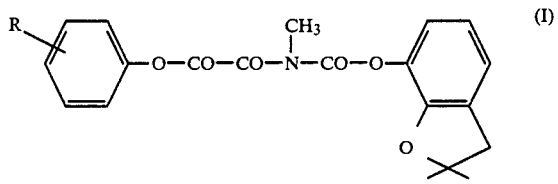

in which

R represents alkyl, alkenyl, alkinyl, alkoxy, alkylthio, halogenoalkyl, halogenoalkoxy, halogenalkylthio, halogen, nitro, dialkylamino, alkylsulphinyl, alkylsulphonyl, cycloalkyl or a saturated, optionally substituted heterocyclic radical with one or more hetero-atoms from the group comprising O, S and N, or forms a ring which is fused onto the phenyl radical, optionally contains one or more hetero-atoms from the group comprising O, S and N and is optionally substituted, have now been found.

It has furthermore been found that the new carbamic acid esters of the formula I are obtained by a process in which 2,3-dihydro-2,2-dimethyl-benzofuran-7-yl N-chlorooxalyl-N-methylcarbamate of the formula II

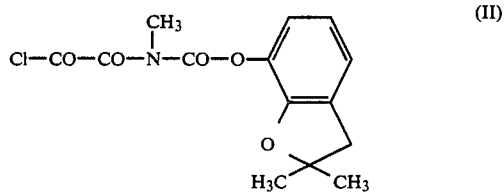

is reacted with phenols of the general formula (III)

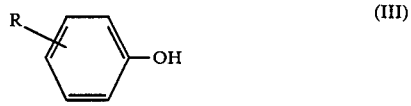

in which

R has the abovementioned meaning, if appropriate in the presence of a diluent and/or if appropriate in the presence of a base.

The compounds according to the invention are distinguished by a good activity as agents for combating pests, in particular as insecticides, acaricides and nematocides.

It is decidedly surprising that they exhibit a more powerful action, coupled with a favorable toxicity to warm-blooded animals, than the oxalyl-N-methylcarbamates known from the prior art.

Formula I provides a general definition of the compounds according to the invention; in this formula, R preferably represents $C_1$-$C_4$-alkyl, $C_2$-$C_4$-alkenyl, $C_1$-$C_4$-alkoxy, $C_1$-$C_4$-alkylthio, $C_1$-$C_4$-halogenoalkyl, $C_1$-$C_4$-halogenoalkoxy or $C_1$-$C_4$-halogenoalkylthio with in each case up to 5 halogen atoms, fluorine, chlorine, bromine, nitro, di-($C_1$-$C_4$-alkyl)-amino, $C_1$-$C_4$-alkylsulphinyl, $C_1$-$C_4$-alkylsulphonyl, $C_3H_8$-cycloalkyl, tetrahydrofuranyl, dioxolanyl, pyrrolidinyl, piperidinyl, morpholinyl or N-methyl-piperazinyl, optionally substituted by $C_1$-$C_4$-alkyl or halogen.

R furthermore preferably forms a saturated 5-membered or 6-membered ring which is fused onto two adjacent C atoms of the phenyl ring, can optionally contain hetero-atoms, such as O, S or N, and is optionally substituted by halogen or $C_1$-$C_4$-alkyl, rings which may be mentioned in particular being: —O—$CH_2$—O—; —O—$CF_2$—O—; O—$CH_2$—$CF_2$—O—; —O—$CF_2$—$CF_2O$—; —O—$CF_2$—O—$CF_2$—; —$CH_2$—C($CH_3$)$_2$—O—, —O—CH($CH_3$)—O—, —O—C($CH_3$)$_2$—O—, —O—CH($CH_3$)—O—, —O—C($CH_3$)$_2$—O—, —$CH_2$—C($CH_3$)$_2$—$CH_2$; —O—$CH_2$—C($CH_3$)$_2$—O, —$CH_2$—O—C($CH_3$)$_2$—O—.

Particularly preferred compounds of the formula I are those in which

R represents methyl, ethyl, propyl, i-propyl, butyl, i-butyl, s-butyl, t-butyl, allyl, methoxy, ethoxy, propoxy, i-propoxy, butoxy, i-butoxy, s-butoxy, t-butoxy, methylthio, chloromethyl, trichloromethyl, trifluoromethyl, trifluoromethoxy, trifluoromethylthio, fluorine, chlorine, bromine, nitro, dimethylamino, diethylamino, methylsulphinyl, methylsulphonyl, cyclopentyl, cyclohexyl, tetrahydrofuranyl, dioxolanyl, dioxanyl, pyrrolidinyl, piperidinyl or morpholinyl, or forms a ring fused onto two adjacent C atoms of the phenyl radical, in which case R represents the following radical:

—O—$CH_2$—O—; —$CH_2$—C($CH_3$)$_2$—O, —O—CH($CH_3$)—O—, —O—C($CH_3$)$_2$—O— or —$CH_2$—C($CH_3$)$_2$—$CH_2$—.

The following compounds are very particularly preferred: the methylphenyl, i-propylphenyl, methoxyphenyl, i-propoxyphenyl, trifluoromethoxyphenyl, chlorophenyl, nitrophenyl, 2,3-dioxomethylenephenyl, 2,3-dioxo-isopropylidenephenyl and 2,3-dihydro-2,2-dimethylbenzofuran-7-yl esters of 2-[N-(2,3-dihydro-2,2-dimethylbenzofuran-7-yl)-oxycarbonyl-N-methyl]-amino-2-oxo-ethanoic acid.

If 2,3-dihydro-2,2-dimethylbenzofuran-7-yl N-chlorooxalyl-N-methylcarbamate (formula IV) and 4-chlorophenol (formula V) are used as starting substances, the course of the reaction can be represented by the following equation:

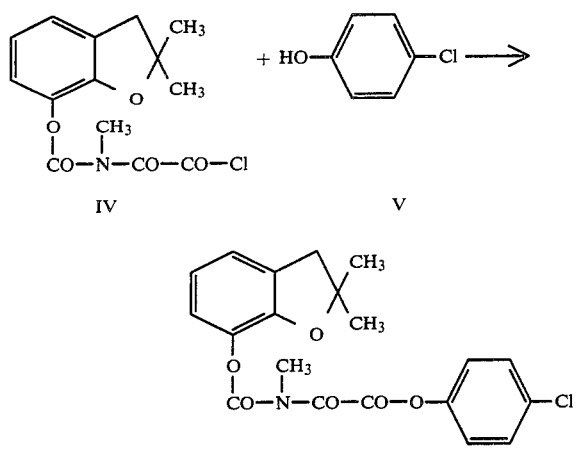

Suitable diluents for the preparation of compounds according to the invention are inert organic solvents. These include ethers, such as diethyl ether, dioxane or tetrahydrofuran, hydrocarbons, such as benzene or toluene, chlorinated hydrocarbons, such as methylene chloride, chloroform or chlorobenzenes, and also nitriles, ketones, esters and mixtures of these solvents.

Bases, such as, for example, sodium carbonate, sodium bicarbonate or tertiary organic bases, such as, for example, triethylamine or benzyldimethylamine, are preferably added to the reaction mixture as acid-binding agents.

The reaction temperature can be varied within a substantial range. In general, the reaction. is carried out between 0°–100° C.

The reactants are usually employed in equimolar amounts, but it is also possible to use one of the components in excess.

The preparation of the N-chlorooxalyl-carbamic acid ester of the formula (II) is known (compare DE-OS (German Published Specification) No. 3,205,195). The phenols required, of the formula (III), are known or can be prepared by known methods.

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma ouadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferna, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp , Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp. Chorioptes spp., Sarcoptes spp., Tarsonemus spp., *Bryobia praetiosa,* Panonychus spp., and Tetranychus spp.

The phytoparasitic nematodes include Pratylenchus spp., *Radopholus similis, Ditylenchus dipsaci, Tylenchulus semipenetrans,* Heterodera spp , Meloidogyne spp , Aphelenchoides spp., Longidorus spp., Xiphinema spp. and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents such as dimethylformamide and dimethylsulphoxide, as well as water; by liquefied gaseous extenders or carriers are meant liquids which are gaseous at normal temperature and under normal pressure, for example aerosol propellants such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the inVention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of veterinary medicine.

The active compounds according to the invention are used in a known manner in the veterinary sector, such as by oral administration, for example in the form of tablets, capsules, drinks and granules, by dermal application, for example in the form of dipping, spraying, pouring on and spotting on, and dusting, and by parenteral administration, for example in the form of an injection.

PREPARATION EXAMPLES

Preparation of the starting compound
2,3-dihydro-2,2-dimethyl-benzofuran-7-yl
N-chlorooxalyl-N-methylcarbamate

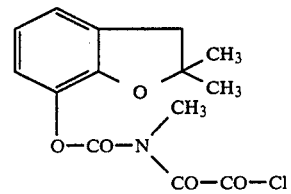

5.4 ml of oxalyl chloride are added to 12.2 g of 2,3-dihydro-2,2-dimethyl-benzofuran-7-yl N-methylcarbamate in 100 ml of toluene and the mixture is then warmed slowly to 60°–80° C. until the evolution of gas has ended (about 4 hours). The solution thus formed can be used for the reaction to give the compounds according to the invention. After the toluene has been distilled off in vacuo, 5 g of a viscous oil remain which, after trituration with diisopropyl ether, crystallizes. Melting point: 91°–93° C., 4.7 g–96% of theory.

4-Chlorophenyl 2-[N-(2,3-dihydro-2,2-dimethylbenzofuran-7-yl)-oxycarbonyl-N-methyl]-amino-2-oxo-ethanoic acid ester

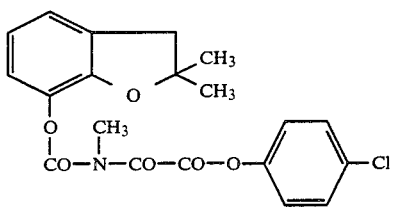

12 8 g of 4-chlorophenol are slowly introduced into 31.1 g of 2,3-dihydro-2,2-dimethylbenzofuran-7-yl N-oxalyl-N-methyl-carbamate in 400 ml of toluene at room temperature, and 13.7 g of triethylamine are then added dropwise. After four hours, the toluene phase is separated off, dried and concentrated and the residue is recrystallized from ethanol. 23 g (57% of theory), melting point: 148°–150° C.

The following oxalyl derivatives were prepared in a corresponding manner:

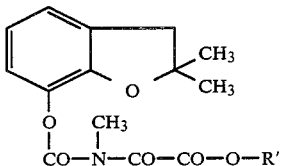

| Type No. | R' | Yield (%) | Melting point (°C.) |
|---|---|---|---|
| 2 | 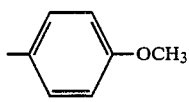 | 93 | 152–154 |
| 3 | 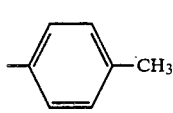 | 94 | 116–118 |
| 4 | 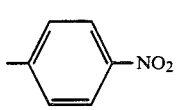 | 86 | 120–125 |
| 5 | 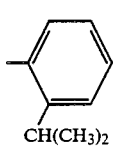 | 47 | 89–90 |
| 6 | (2,6-dimethylphenyl isopropylidene) | 83 | 123–126 |
| 7 | (2-isopropoxyphenyl) | 80 | 125–127 |

EXAMPLE A

Test insect: Phorbia antiqua maggots (in the soil)
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior action compared with the prior art: 1, 3, 4, 5 and 6.

EXAMPLE B

Long-term action test/soil insects
Test insect: Phorbia antiqua maggots
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (mg/l), being decisive. The soil is filled into 5 liter pots and these are left to stand at 20° C.

After an interval of 2 weeks, and after prior renewed thorough mixing, soil samples of 250 cc are taken and the corresponding test insects are placed in the treated soil. After a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior action compared with the prior art: 1, 3, 5 and 6.

It will be understood that the specification and examples are illustrative but not limitative of the present invention and that other embodiments within the spirit and scope of the invention will suggest themselves to those skilled in the art.

We claim:

1. An N-oxalyl-N-methyl-carbamic acid ester of the formula

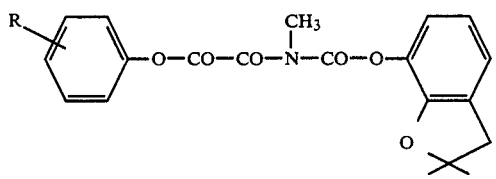

in which R represents 4-methyl, 2-isopropyl, 4-chlorine or —CH$_2$—C(CH$_3$)$_2$—O—.

2. A compound according to claim 1, wherein such compound is 4-chlorophenyl 2-[N-(2,3-dihydro-2,2-dimethylbenzofuran-7-yl)-oxycarbonyl-N-methyl]-amino-2-oxo-ethanoic acid ester of the formula

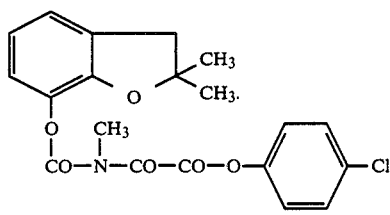

3. A compound according to claim 1, wherein such compound is 4-methylphenyl 2-[N-(2,3-dihydro-2,2-dimethylbenzofuran-7-yl)-oxycarbonyl-N-methyl]-amino-2-oxo-ethanoic acid ester of the formula

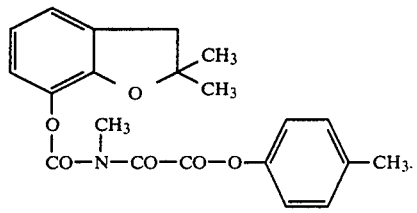

4. A compound according to claim 1, wherein such compound is 2-isopropylphenyl 2-[N-(2,3-dihydro-2,2-dimethylbenzofuran-7-yl)-oxycarbonyl-N-methyl]-amino-2-oxo-ethanoic acid ester of the formula

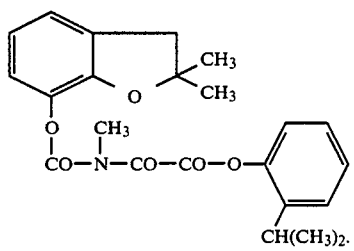

5. A compound according to claim 1, wherein such compound is 2,2-dimethylbenzofuran-7-yl 2-[N-(2,3-dihydro-2,2-dimethyl-benzofuran-7-yl)-oxycarbonyl-N-methyl]-amino-2-oxzo-ethanoic acid ester of the formula

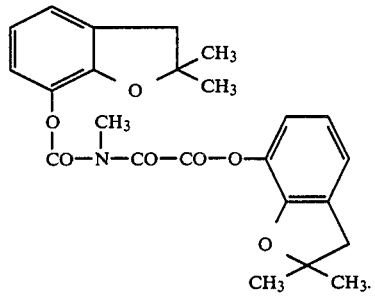

6. An insecticidal, arachnicidal and nematocidal composition comprising an insecticidally, arachnicidally and nematocidally effective amount of a compound according to claim 1 in admixture with a diluent.

7. A method of combating insects, arachnids and nematodes which comprises applying thereto or to a habitat thereof an insecticidally, arachnicidally or nematicidally effective amount of a compound according to claim 1.

8. The method according to claim 7, wherein such compound is
  4-chlorophenyl 2-[N-(2,3-dihydro-2,2-dimethylbenzofuran-7-yl)-oxycarbonyl-N-methyl]-amino-2-oxo-ethanoic acid ester,
  4-methylphenyl 2-[N-(2,3-dihydro-2,2-dimethylbenzofuran-7-yl)-oxycarbonyl-N-methyl]-amino-2-oxo-ethanoic acid ester,
  2-isopropylphenyl 2-[N-(2,3-dihydro-2,2-dimethylbenzofuran-7-yl)-oxycarbonyl-N-methyl]-amino-2-oxo-ethanoic acid ester,
  2,2-dimethylbenzofuran-7-yl 2-[N-(2,3-dihydro-2,2-dimethyl-benzofuran-7-yl)-oxycarbonyl-N-methyl]-amino-2-oxo-ethanoic acid ester.

* * * * *

UNITED STATES PATENT AND TRADEMARK OFFICE
CERTIFICATE OF CORRECTION

PATENT NO. : 4,616,035
DATED : October 7, 1986
INVENTOR(S) : Gerhard Heywang, et al.

It is certified that error appears in the above-identified patent and that said Letters Patent are hereby corrected as shown below:

Col. 4, lines 7, 8　　　　Correct spelling of --quadrata--
Col. 6, line 6　　　　　　Correct --invention--.
Col. 6, line 68　　　　　Delete "5 g" and substitute --15 g--
Col. 7, line 2　　　　　　Delete "-" before "96%" and substitute -- = --
Col. 7, line 20　　　　　Delete "12 8" and substitute --12.8--
Col. 10, line 30　　　　Delete "oxzo" and substitute --oxo--
Col. 10, line 64　　　　"ester," should read --ester of--.

Signed and Sealed this

Twenty-seventh Day of January, 1987

Attest:

DONALD J. QUIGG

Attesting Officer　　　　Commissioner of Patents and Trademarks